United States Patent
Naderlinger

[11] Patent Number: 5,720,764
[45] Date of Patent: Feb. 24, 1998

[54] VENA CAVA THROMBUS FILTER

[76] Inventor: Eduard Naderlinger, Freesienweg 1, 50127 Bergheim, Germany

[21] Appl. No.: 750,517

[22] PCT Filed: Jun. 10, 1995

[86] PCT No.: PCT/EP95/02244

§ 371 Date: Dec. 11, 1996

§ 102(e) Date: Dec. 11, 1996

[87] PCT Pub. No.: WO95/34254

PCT Pub. Date: Dec. 21, 1995

[30] Foreign Application Priority Data

Jun. 11, 1994 [DE] Germany ............ 94 09 484 U

[51] Int. Cl.$^6$ .................................. A61M 29/00
[52] U.S. Cl. ......................... 606/200; 606/127
[58] Field of Search ................... 606/200, 159, 606/151, 170, 191, 194, 108

[56] References Cited

U.S. PATENT DOCUMENTS

| | | | |
|---|---|---|---|
| 5,222,971 | 6/1993 | Willard et al. | 606/200 |
| 5,330,482 | 7/1994 | Gibbs et al. | 606/127 |
| 5,496,330 | 3/1996 | Bates et al. | 606/127 |

FOREIGN PATENT DOCUMENTS

| | | |
|---|---|---|
| 0117940 | 9/1984 | European Pat. Off. |
| 0165713 | 12/1985 | European Pat. Off. |
| 0472334 | 2/1992 | European Pat. Off. |
| 0521222 | 1/1993 | European Pat. Off. |
| 0598635 | 5/1994 | European Pat. Off. |
| 2643250 | 8/1990 | France |
| 2652267 | 3/1991 | France |
| 3039174 | 6/1981 | Germany |
| 3417738 | 10/1986 | Germany |
| 9109006 | 11/1991 | Germany |
| 4038206 | 2/1992 | Germany |

*Primary Examiner*—Michael Buiz
*Assistant Examiner*—Kevin Truong
*Attorney, Agent, or Firm*—Friedrich Kueffner

[57] ABSTRACT

A vena cava thrombus filter includes a catheter for insertion in a vein including a tube of flexible plastic and a guiding and holding wire supported and axially displaceable in the tube. The distal end of the wire has a filter element formed of wires which are elastically expandable inside a vein, wherein, in a forwardly pushed position outside of the catheter insertion end, the wires can expand to form a basket through which liquid can flow. The catheter has at the handling end of the guiding and holding wire a handle, and a fitting closable to irrigation fluid provided with a bayonet lock for fastening the handle relative to the fitting. The fitting has a metallic guide sleeve, wherein the flexible tube of the catheter is pulled over the metallic guide sleeve. A flexible rubber or plastic sleeve is arranged over the metallic guide sleeve and the flexible tube pulled over the metallic guide sleeve.

5 Claims, 1 Drawing Sheet

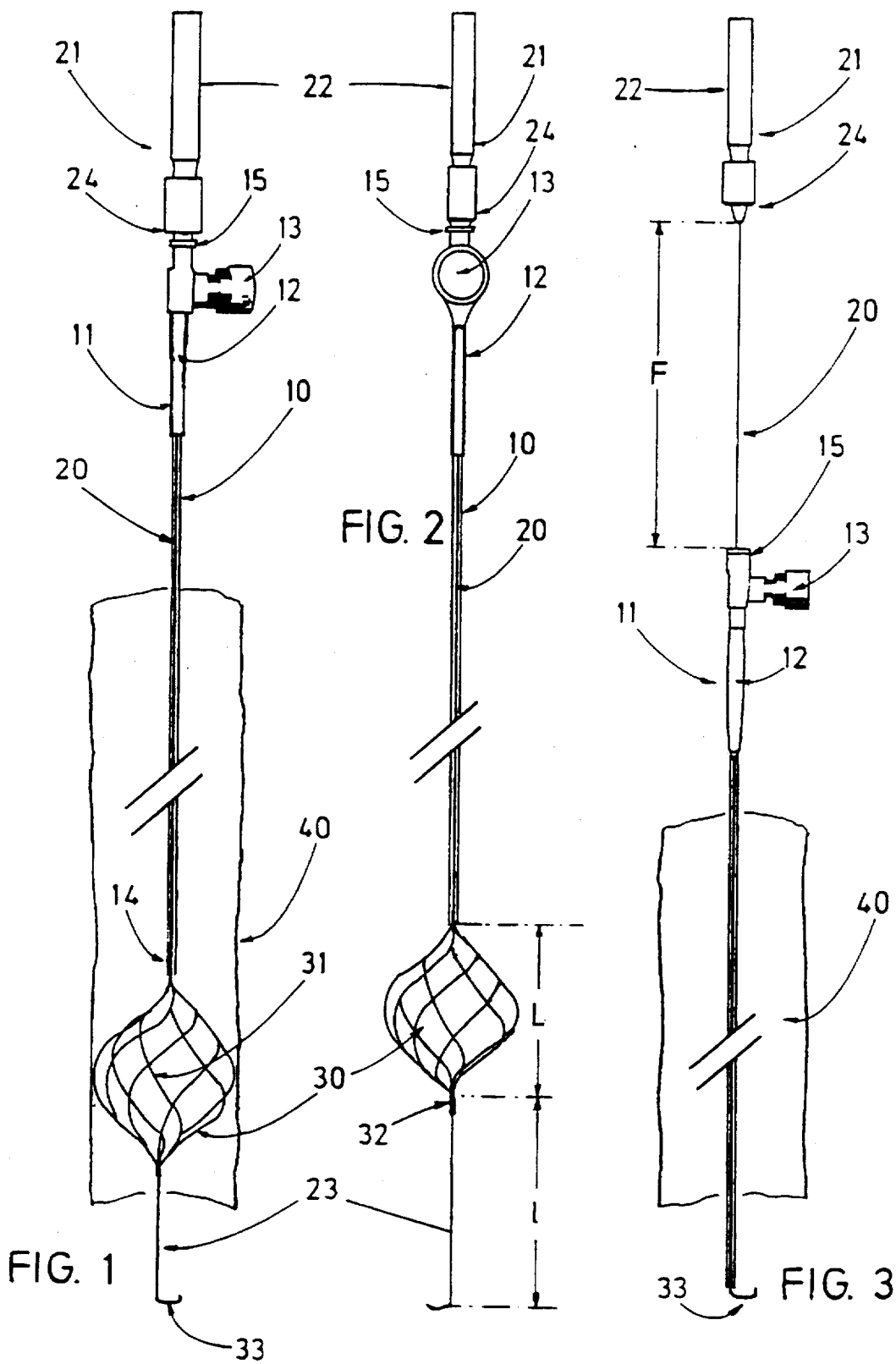

5,720,764

VENA CAVA THROMBUS FILTER

BACKGROUND OF THE INVENTION

1. Field of the Invention

The invention is directed to a vena cava thrombus filter with a catheter for insertion in a vein, this catheter having a tube of flexible plastic with a guiding and holding wire supported therein so as to be displaceable axially, its insertion end having a filter element formed of thin wires which can expand elastically inside a vein and which, in the pushed forward position outside of the catheter insertion end, expand to form a basket through which liquid can flow.

Insertion of a vena cava filter is indicated absolutely, for example, with thrombolyses for temporary prophylaxis of pulmonary emboli due to detaching thrombi or fragments of such thrombi.

2. Description of the Prior Art

Known devices for intercepting and/or removing such thrombi in the blood circulation are usually made of plastic and can kink when loaded, causing impairment of function. Known vena cava thrombus filters are also often complicated in construction and handling.

A device for filtering blood in the blood vessels of a patient is known from EP-A-0 472 334. It comprises a catheter with a guiding and holding wire which is supported therein so as to be displaceable axially. An expandable filter element formed of a plurality of wires which can expand to form a basket is arranged at the distal end of the guiding and holding wire. The wires can open out or draw together depending on the axial displacement of the guide wire inside the blood vessel relative to the filter.

EP-A-0 117 940 describes a similar device with a thrombus filter at the distal end of a catheter which can be introduced in a vein. In this device the filter element is formed of memory wires which can be curled up into loops and which can be collapsed when inserted into the vein by stretching the guide wire or expanded in the vein to form loops by the opposite movement of the guide wire. A liquid may be injected into the vein through the catheter via a branch of the fitting at the guide end.

SUMMARY OF THE INVENTION

The object of the present invention is to provide an improved temporary vena cava thrombus filter with a catheter for insertion in a vein by means of which detaching thrombi or fragments thereof can be filtered out of the blood circulation in cases of thrombolysis, thrombectomy or pregnancy entailing risk so as to safely prevent the risk of pulmonary embolism. The filter is designed to enable optional access via all known routes of access, e.g., veins of the arm (basilic vein, brachial vein, jugular vein, subclavian vein, femoral vein). Accordingly, the catheter must be very thin and flexible like an angiogram catheter so that it can remain in place for the duration of clot fragmentation or lysis.

According to the invention, a vena cava thrombus filter is provided which includes a catheter for insertion in a vein including a tube of flexible plastic and a guiding and holding wire supported and axially displaceable in the tube. The distal end of the wire has a filter element formed of wires which are elastically expandable inside a vein, wherein, in a forwardly pushed position outside of the catheter insertion end, the wires can expand to form a basket through which liquid can flow. The catheter has at the handling end of the guiding and holding wire a handle, and a fitting closable to irrigation fluid provided with a bayonet lock for fastening the handle relative to the fitting. The fitting has a metallic guide sleeve, wherein the flexible tube of the catheter is pulled over the metallic guide sleeve. A flexible rubber or plastic sleeve is arranged over the metallic guide sleeve and the flexible tube pulled over the metallic guide sleeve. This object is met in a vena cava thrombus filter having a catheter for insertion in a vein by its construction corresponding to the characterizing features of claim 1.

It is very advantageous that all important veins and vein branches can be accessed by the vena cava thrombus filter in its closed state in which the flexible wires are folded together when retracted into the distal end of the catheter tube. The actual filter element is pushed out of the end of the catheter tube and brought into the expanded position after it has been successfully positioned by operating the guiding and holding wire and after this position has been checked by X-ray. In so doing, the elastically expandable wires unfold to form the basketlike filter element which is suitable for stopping and trapping thrombi or fragments thereof floating in the blood circulation.

Further advisable constructions of the vena cava thrombus filter are indicated in the subclaims.

A preferred embodiment form of the invention is shown in schematic drawings. Further advantageous features of the invention can be seen from the drawings.

DESCRIPTION OF THE DRAWINGS

FIG. 1 is a side view of a vena cava thrombus filter with extended elastically expanded filter element;

FIG. 2 is a front view in partial section showing the thrombus filter with extended and expanded filter element;

FIG. 3 is a side view of the thrombus filter retracted into the catheter for insertion in a vein.

DESCRIPTION OF THE PREFERRED EMBODIMENTS

The vena cava thrombus filter shown in FIG. 1 has a filter element (30) which telescopes out of the insertion end (14) after insertion in a vein (40) and which, after exiting the insertion end (14), expands to form a basket as a result of the elasticity of the thin, expandable wires (31).

Before using the vena cava filter according to the invention, a Seldinger needle is first introduced into an arm vein and a short guide wire is pushed through the needle which is then removed over the guide wire. A commercially available 5-F sluice or lock is then implanted in the vein and the guide wire with dilator is removed. The guide end (14) of the catheter (10) is now pushed through the lock into the vein with the filter element (30) in the retracted state.

As will be seen from consideration of FIGS. 1 to 3 together, the catheter (10) is a tube of flexible plastic with a guiding and holding wire (20) supported therein so as to be displaceable axially. A handle (22) by which the filter element (30) can be retracted or extended is provided at the handling end (21) of the guiding and holding wire (20). The catheter (10) is moved and the filter element (30) is closed and opened by pulling out and pushing in the handle (22), respectively. For example, FIGS. 1 and 2, in which the guide wire (20) is pushed in, show the filter element (30) which is telescoped out of the catheter end (14) and expanded to form a basket due to the elasticity of the wires (31) which are expandable into a helical shape. FIG. 3 shows the retracted state resulting when the handle (22) of the catheter (10) is pulled out. In the expanded state, the filter element (30)

operates like a liquid-permeable sieve in the shape of a basket (30). It is formed of a plurality of implant-quality memory wires (31), preferably eight wires with a diameter of roughly 0.08 mm which can expand in a bulging helical shape.

In an advisable embodiment, a sleeve (32) is arranged at the end of the wire basket (30) forming the filter, a Teflon-coated guide wire (23) with a "J" tip (33) being fastened thereto.

In another advisable construction, the catheter (10) is covered with a flexible rubber or plastic sleeve (12) at its handling end (21) over the metallic guide sleeve of the fitting (13) and the catheter tube (10) which is drawn over the latter. The fitting (13) can be closed for an irrigating fluid. Further, fitting (13) has means (15) to which the handle (22) of the guiding and holding wire (20) can be fastened by a quarter-turn fastener or bayonet lock (24).

For reliable insertion of the filter element (30) in veins of larger diameter, this filter element (30) has a diameter of approximately 35 mm and a length of approximately 55 mm. However, it can be seen that the filter element (30) easily adapts to any vein diameter due to the extraordinary elasticity of its extremely thin wires (31) and can also be used in very thin veins. In a particularly advantageous manner, it is implanted by means of a commercially available 5-F lock.

Dependable operation by pulling out and pushing in the guiding and holding wire (20) is achieved in that the wire (20) has a free axial path (F) with reference to the surrounding catheter tube (10) as is shown in FIG. 3 and this free path (F) corresponds at least to the length (L) of the expanded filter (30) plus the length (1) of sleeve (32) arranged at the end, including the Teflon-coated "J"-wire tip (33).

The temporary vena cava filter according to the invention which is constructed as described above meets all requirements for optimum thrombolysis protection. It enables optional access via all known access routes, e.g., arm veins, is very thin, e.g., the outer diameter of the catheter is 1.5 to 2 mm, and extremely flexible. It is suitable for all cava sizes and can also be placed in the iliac vein. In addition, the type of construction and fastening possibility offered by the bayonet lock (24) enables a longer placement time for the duration of lysis. The integrated "J" guide wire tip also greatly facilitates placement.

In sum, the vena cava thrombus filter of the invention with the catheter for insertion in a vein presents an optimum solution to the problem indicated in the above statement of purpose.

I claim:

1. A vena cava thrombus filter comprising a catheter for insertion in a vein, the catheter comprising a tube of flexible plastic and a guiding and holding wire axially displaceably supported in the tube of flexible plastic, the guiding and holding wire having a handling end and a distal end, the distal end having a filter element formed of wires configured to be elastically expandable inside a vein, wherein, in a forwardly pushed position outside of an insertion end of the catheter, the wires are expandable to form a basket through which liquid can flow, further comprising a handle mounted at the handling end of the guiding and holding wire, a fitting closable to irrigation fluid and having means comprising a bayonet lock for fastening the handle relative to the fitting, the fitting further having a metallic guide sleeve, the flexible tube of the catheter being pulled over the metallic guide sleeve, and a flexible rubber or plastic sleeve being arranged over the metallic guide sleeve and the flexible tube of the catheter pulled over the metallic guide sleeve.

2. The vena cava thrombus filter according to claim 1, further comprising a metal sleeve arranged at a distal end of the wires forming the filter element, and a Teflon-coated guide wire having a Teflon-coated J-shaped guide wire tip being fastened to the metal sleeve, wherein the guiding and holding wire is axially displaceable in the tube of flexible plastic by a distance which is at least equal to a combined length of the basket and of the metal sleeve and the Teflon-coated guide wire.

3. The vena cava thrombus filter according to claim 1, wherein the basket formed by the wires has a diameter of approximately 35 mm and a length of approximately 55 mm.

4. The vena cava thrombus filter according to claim 3, wherein the basket comprises a plurality of implant-quality memory wires capable of opening up into a bulging helical shape.

5. The vena cava thrombus filter according to claim 4, comprising eight memory wires having a diameter of 0.08 mm.

* * * * *